Figure 1:
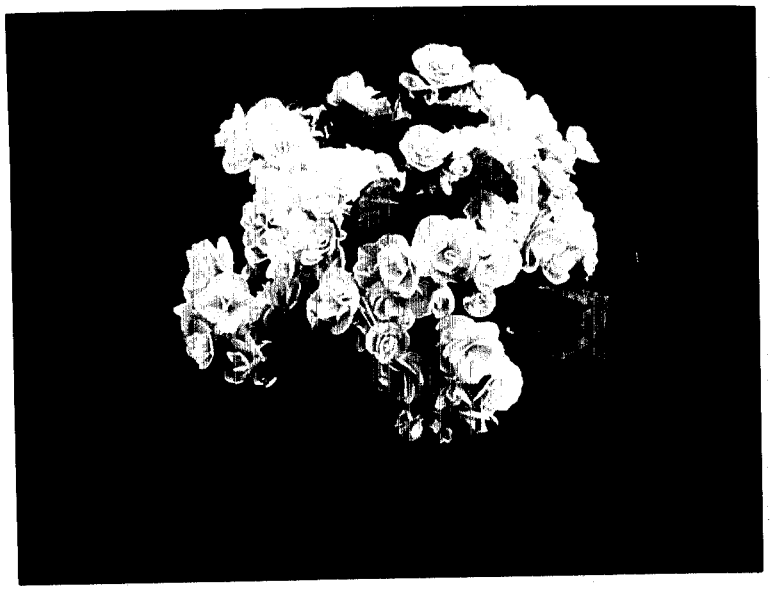
Figure 2:
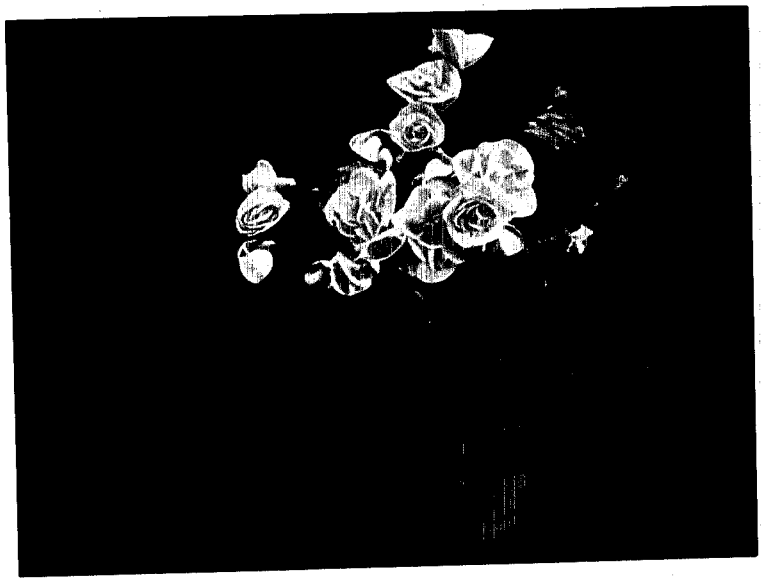
Figure 3:
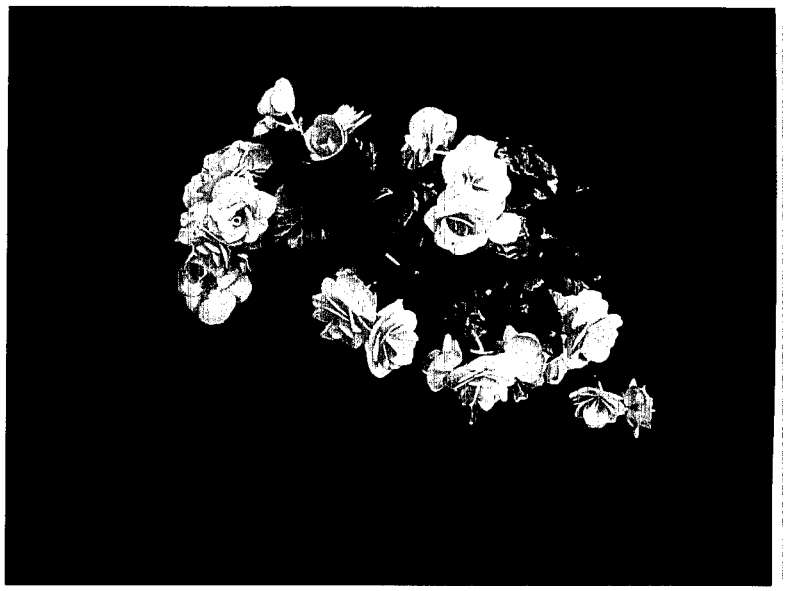

United States Patent [19]

Man

[11] Patent Number: Plant 7,404

[45] Date of Patent: Dec. 25, 1990

[54] BEGONIA CULTIVAR MANIFESTO

[75] Inventor: Jan Man, Amselveen, Netherlands

[73] Assignee: Gebr. Man C.V., Netherlands

[21] Appl. No.: 329,118

[22] Filed: Mar. 27, 1989

[51] Int. Cl.[5] ..... A01H 5/00

[52] U.S. Cl. ..... Plt./68

[58] Field of Search ..... Plt./68

[56] References Cited

U.S. PATENT DOCUMENTS

P.P. 5,746 5/1986 Rohde ..... Plt. 68

*Primary Examiner*—Howard J. Locker

*Attorney, Agent, or Firm*—Renner, Otto, Boisselle & Sklar

[57] ABSTRACT

A Begonia plant named Manifesto characterized by its double flower form and pink flower color.

2 Drawing Sheets

1

The present invention relates to a new and distinctive cultivar of Begonia plant, botanically known as Begonia Hiemalis, Fotsch, and known by the cultivar name Manifesto.

The cultivar Manifesto is a mutant from the parent cultivar known by the cultivar name Manderijn, differing from Manderijn primarily in the color of its flower, Manderijn being in the red color group (39B R.H.S. Color Chart) while the cultivar Manifesto is pink, 54B on The Royal Horticultural Society color chart.

The cultivar Manifesto has been asexually reproduced at Oberlin, Ohio by stem and/or leaf cuttings and has reproduced its unique features through successive propagations.

The accompanying color photograph illustrates in perspective view the overall appearance of the cultivar Manifesto.

The following is a description of the new variety Manifesto, the color terminology being in accordance with The Royal Horticultural Society Color chart.

2

Manifesto was originally produced as a mutation of the parent variety, Manderijn, differing from Manderijn in the color of the flower. When grown in a four (4) inch pot, Manifesto grows to medium or average height and is of medium width. The upper side of its leaves are dark green while the lower sides are reddish green. The leaf blades are closed at their bases with bi-crenate incisions along the margins. The leaves undulate at their margins only slightly.

Manifesto has double flowers, with the inner petal color of the middle of the upper side thereof being red 54B on the R.H.S. Color Chart. The flowers are two to three (2–3) inches in diameter and change petal size gradually. The petal edges are smooth with no incisions. The inflorescence density of Manifesto is medium.

I claim:

1. A new and distinct cultivar of Begonia plant named Manifesto as described and illustrated, and particularly characterized by its red flower color and its double flower form.

* * * * *